US00RE46425E

(19) United States
(12) Reissued Patent
Eggink et al.

(10) Patent Number: US RE46,425 E
(45) Date of Reissued Patent: Jun. 6, 2017

(54) PRO-ANGIOGENIC PEPTIDES AND USES THEREOF

(71) Applicant: Susavion Biosciences, Inc., Tempe, AZ (US)

(72) Inventors: Laura L. Eggink, Scottsdale, AZ (US); J. Kenneth Hoober, Phoenix, AZ (US)

(73) Assignee: Susavion Biosciences, Inc., Tempe, AZ (US)

(21) Appl. No.: 14/734,785

(22) Filed: Jun. 9, 2015

Related U.S. Patent Documents

Reissue of:
(64) Patent No.: 8,460,697
Issued: Jun. 11, 2013
Appl. No.: 12/823,556
Filed: Jun. 25, 2010

U.S. Applications:
(63) Continuation-in-part of application No. 11/955,143, filed on Dec. 12, 2007, now Pat. No. 7,838,497.

(60) Provisional application No. 61/221,021, filed on Jun. 29, 2009, provisional application No. 60/869,862, filed on Dec. 13, 2006.

(51) Int. Cl.
*A61K 38/08* (2006.01)
*C07K 7/06* (2006.01)
*C07K 14/00* (2006.01)

(52) U.S. Cl.
CPC ..... *C07K 14/001* (2013.01); *C07K 7/06* (2013.01)

(58) Field of Classification Search
CPC ..... C07K 14/001; C07K 7/06
USPC ..... 424/443; 514/13.3, 18.7, 21.8, 9.4; 530/329, 330
See application file for complete search history.

(56) References Cited

U.S. PATENT DOCUMENTS

| | | | | |
|---|---|---|---|---|
| 5,641,747 | A | 6/1997 | Popoff et al. | |
| 5,677,276 | A | 10/1997 | Dickerson et al. | |
| 5,910,310 | A | 6/1999 | Heinen et al. | |
| 5,919,998 | A | 7/1999 | Bandurski et al. | |
| 6,159,937 | A | 12/2000 | Larsen et al. | |
| 6,193,981 | B1 | 2/2001 | Goldstein | |
| 6,551,795 | B1 | 4/2003 | Rubenfield et al. | |
| 7,105,481 | B2 | 9/2006 | Uutela et al. | |
| 7,838,497 | B2 * | 11/2010 | Eggink et al. | 514/9.4 |
| 8,034,773 | B2 * | 10/2011 | Eggink | C07K 14/57 435/69.1 |
| 9,155,796 | B2 * | 10/2015 | Eggink | A61K 47/48176 |
| 2003/0073637 | A1 | 4/2003 | Uutela et al. | |
| 2004/0031072 | A1 | 2/2004 | La Rosa et al. | |
| 2005/0063937 | A1 | 3/2005 | Li et al. | |
| 2006/0024668 | A1 | 2/2006 | Hoek | |
| 2006/0148093 | A1 | 7/2006 | Gygi et al. | |
| 2006/0160730 | A1 | 7/2006 | Cuttitta et al. | |
| 2006/0287234 | A1 | 12/2006 | Breen et al. | |
| 2007/0021342 | A1 | 1/2007 | Breen et al. | |
| 2007/0149475 | A1 | 6/2007 | Murray et al. | |
| 2007/0154448 | A1 | 7/2007 | Reid et al. | |
| 2008/0102076 | A1 | 5/2008 | Eggink et al. | |
| 2009/0041793 | A1 | 2/2009 | Eggink et al. | |

FOREIGN PATENT DOCUMENTS

| | | |
|---|---|---|
| WO | 96/40903 | 12/1996 |
| WO | 00/31130 | 6/2000 |
| WO | 02/058589 | 8/2002 |
| WO | 03/091275 | 11/2003 |
| WO | 2004/011650 | 5/2004 |
| WO | 2005/017133 | 2/2005 |
| WO | 2005/087793 A2 | 9/2005 |
| WO | 2006/063028 | 6/2006 |
| WO | 2006/105021 A2 | 10/2006 |

OTHER PUBLICATIONS

Chargelegue et al., "A Peptide Mimic of a Protective Epitope of Respiratory Syncytial Virus Selected from a Combinatorial Library Induces Virus-Neutralizing Antibodies and Reduces Viral Load in Vivo," *J. of Virology*, 72(3):2040-2046 (Mar. 1998).
Ciesielski et al., "Cellular antitumour immune response to a branched lysine multiple anitgenic peptide containing epitopes of a common tumor-specific antigen in a rat glioma model," *Cancer Immunol. Immunother.*, 54:107-119 (2005).
Chersi et al., "Specificities of rabbit antisera to multiple antigen (MAP) peptides," *J. of. Biosciences*, 50(9-10):735-738 (Sep. 1, 1995) Abstract only.
Eggink et al., "A biologically active peptide mimetic of N-acetylgalactosamine/galactose," *BMC Research Notes*, 2:23 (2009).
European Search Report for European Patent Application No. 07869233.2 dated May 11, 2010.
International Search Report for PCT/US2005/003766 dated Apr. 5, 2006.
International Search Report for PCT/US2005/044215 dated Nov. 16, 2006.
International Search Report for PCT/US2007/087413 dated Jul. 29, 2008.
Manki et al., "Vaccination with Multiple Antigen Peptide as Rejection Antigen Peptide in Murine Leukemia," *Cancer Res.*, 58:1960-1964 (May 1, 1998).
Nicolaus, "Symbiotic Approach to Drug Design," *Decision Making in Drug Research*, pp. 173-186 (Jan. 1, 1983).
Olszewska et al., "Protection against Measles Virus-Induced Encephalitis by Anti-mimotope Antibodies: The Role of Antibody Affinity," *Virology*, 272(1):98-105 (Jun. 20, 2000).
Sarig, et al., "Telomeric and Tetraplex DNA Binding Properties of qTBP42: A Homoloque of the CArG Box Binding Protein CBF-A," *Biochem. and Biophys. Res. Comm*, 237(3):617-623 (1997).
Supplementary European Search Report for European Application No. 07871699.0 dated May 17, 2010.

(Continued)

*Primary Examiner* — Shri Ponnaluri
(74) *Attorney, Agent, or Firm* — Rodney J. Fuller; Booth Udall Fuller, PLC

(57) ABSTRACT

This present invention is directed to peptides, compositions, and methods for modulating endogenous cytokine expression in a subject. More specifically, the invention provides peptides useful in regulating the release of a specific pattern of cytokines that promote angiogenesis and/or can be used to modulate the immune system of a subject.

17 Claims, 2 Drawing Sheets

(56) References Cited

OTHER PUBLICATIONS

Written Opinion of the International Searching Authority for PCT/US2005/003766 dated Apr. 5, 2006.
Written Opinion of the International Searching Authority for PCT/US2005/044215 dated Nov. 16, 2006.
Written Opinion of the International Searching Authority for PCT/US2007/087413 dated Jul. 29, 2008.
Written Opinion of the International Searching Authority for PCT/US2007/087425 dated Aug. 5, 2008.
Office Action dated Oct. 23, 2012 in Japanese Application No. 2009-541590 (English translation) (6 pages).

* cited by examiner

FIG. 1
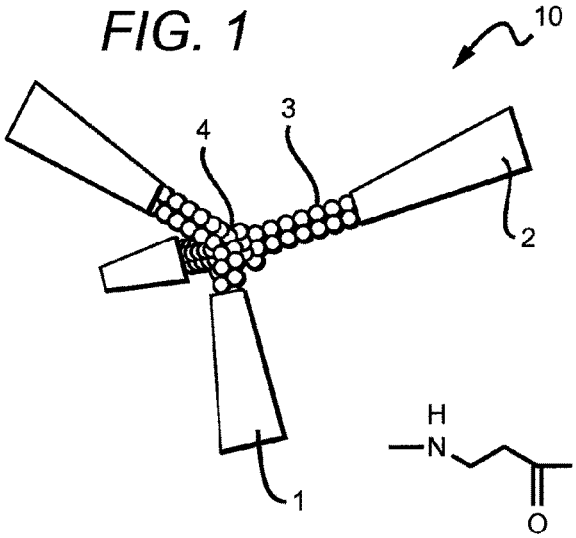
FIG. 3
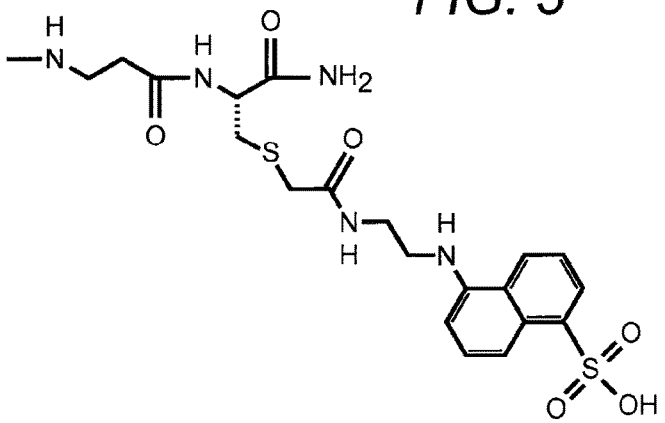
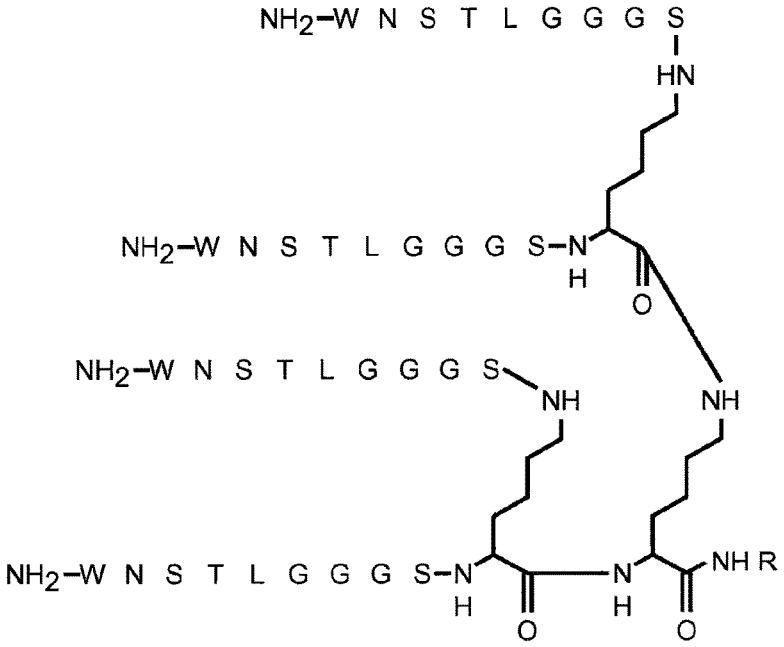
FIG. 2A

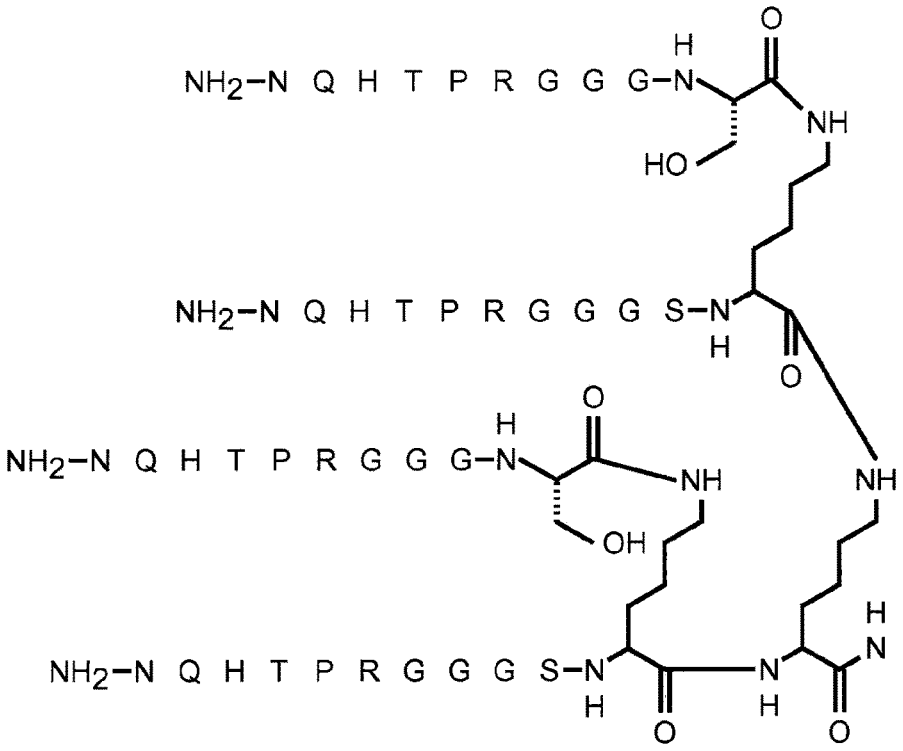
FIG. 2B
FIG. 4
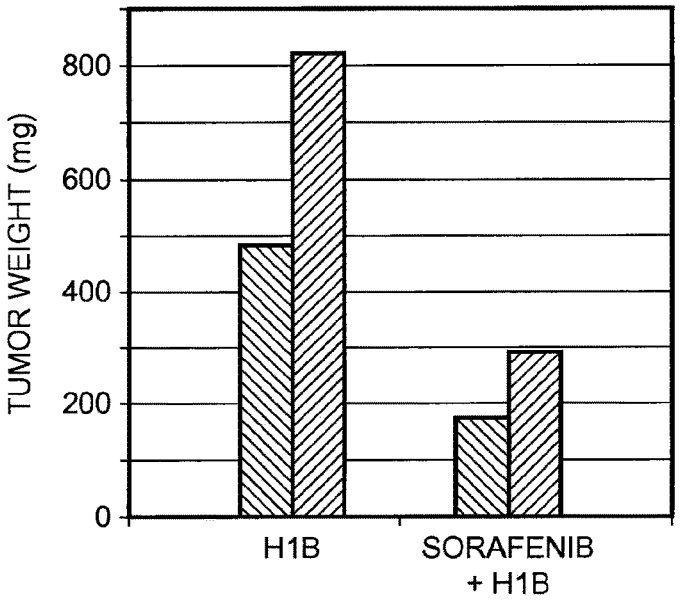

PRO-ANGIOGENIC PEPTIDES AND USES THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

The present application *is a reissue application of U.S. Pat. No. 8,460,697 B2, which* is related to and claims the benefit of U.S. Provisional Application No. 61/221,021 filed Jun. 26, 2009[, and]*; U.S. Pat. No. 8,460,697 B2* is *also* a continuation-in-part of U.S. patent application Ser. No. 11/955,143 filed Dec. 12, 2007, which in turn claims the benefit of U.S. Provisional Application No. 60/869,862 filed Dec. 13, 2006, the contents of each of which are incorporated herein by reference thereto.

*Notice: More than one reissue application has been filed for the reissue of U.S. Pat. No. 8,460,697 B2. The reissue applications are application Ser. No. 14/734,785 (the present application) and Ser. No. 15/278,016, all of which are divisional reissues of U.S. Pat. No. 8,460,697 B2.*

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One [1650] *2,148* byte ASCII (text) file named "Seq_List" created on [Jun. 25, 2010] *June. 9, 2015.*

FIELD OF THE INVENTION

The present invention relates to the fields of therapeutic peptides and endogenous cytokine modulation. More specifically the invention relates to the fields of angiogenesis, wound healing, and/or immune system modulation.

BACKGROUND

Impaired circulation is an underlying aspect of many clinically-manifested disorders including peripheral arterial disease (PAD), ischemic heart disease and chronic wounds. More than 24 million patients are afflicted with these conditions in the US, with 10 million affected by PAD alone. PAD is often a result of diabetes, which currently affects one in three adults over the age of 40 and whose incidence is expected to increase as a result of increasing obesity in the general population. Chronic wounds affect more than 6.5 million patients each year and cause significant impairment of quality of life. Even with current treatments, about 35,000 limb amputations are performed each year due to life-threatening ischemia.

Wound healing after injury occurs in three major stages. First is the hemostatic and inflammatory stage, which minimizes blood loss and recruits specific cells to the site of injury. Platelets engage the injured tissue, initiate clot formation and release growth factors during this first stage. In the second stage, recruited phagocytic cells such as macrophages and monocytes digest the injured tissue and angiogenic growth factors released by activated platelets, macrophages, and other cells bind to receptors on the surface of endothelial cells in pre-existing blood vessels. The endothelial cells then proliferate, migrate into a wound bed, and differentiate into arterial and venous vascular tissue. Finally, in a third remodeling stage, new blood vessels mature by recruiting smooth muscle cells to stabilize the vasculature architecture, whereupon blood begins to flow through the new blood vessels.

Angiogenesis, the process of growth of new blood vessels, is an essential process in wound healing and for restoring blood flow to tissues after injury. The discovery of growth factors that stimulate this process has had a major influence on medical treatment of crippling and life-threatening conditions resulting from loss of blood circulation. At least 20 growth factors have been identified that stimulate angiogenesis. The growth factor most widely studied, and used clinically, is the pro-angiogenic platelet-derived growth factor-BB (PDGF-BB). PDGF is released from many cell types including activated platelets, activated macrophages, endothelial cells, fibroblasts and tumor cells, and PDGF was approved by the FDA in December 1997 for clinical use as a topical agent for diabetic foot ulcers. A second growth factor developed for clinical use is the vascular endothelial growth factor (VEGF). Growth factors of this type and biologically active analogs are typically mid-sized proteins which can be produced by recombinant techniques (e.g. in yeast), and activation of angiogenesis by growth factors is accomplished, at least in part, by stimulation of cytokine production.

IL-8 is a cytokine that activates neutrophils and has potent chemotactic activity on neutrophils and lymphocytes. The inflammatory event at the site of infection or injury activates monocytes and macrophages, which release IL-8. Inflamed endothelial tissue also releases IL-8, which attracts neutrophils from blood into the tissue during the initial phase of the defense mechanism. The consequence is a vicious cycle of recruitment of neutrophils in response to IL-8, damage to tissues, and more production of IL-8 leading to deleterious inflammation as a side effect. In addition, neutrophils adhere to inflamed endothelial tissues through integrins secreted from the cells, and ICAM-1 can stimulate release of the integrins to which neutrophils bind, thereby increasing the level of deleterious inflammation at the site of injury even further. Increased levels of certain types of clinically deleterious cytokines, such as IL-8 and ICAM-1, at a site of infection or injury can therefore cause deleterious side effects which can hinder the process of healing.

The healing of wounds in mammalian tissue may be enhanced by the application, either alone or in combination with a cytokine and/or growth factor, of certain neuropeptides such as Tachykinins, Substance P, Substance K, and the like as well as calcitonin gene-related peptides. The use of such peptides for clinical applications has, however, been hampered by several problematic issues including deleterious side effects. Substance P, for example, is a known mediator of pain impulses and its effects on wound healing have been known for several years. However, Substance P has also been shown to stimulate neurons to release factors that recruit inflammatory cytokines and neutrophils to the site of a wound, thereby causing pain and inflammation.

Therefore, the use of peptides or growth factors and their analogs as therapeutic agents for wound healing can be problematic for a number of reasons, including efficacy, cost, and deleterious side effects such as inflammation. Information relevant to attempts to address one or more of these problems can be found in the following references:

U.S. Pat. No. 7,105,481, U.S. Patent Application No. 2007/0021342, and U.S. Patent Application No. 2007/0154448. However, each one of these references suffers from one or more of the following disadvantages:

1. the requirement for expression of a polynucleotide containing the nucleotide sequence encoding the protein, which can complicate production and significantly increase costs;
2. the requirement for purification of expressed proteins from the other proteins of the host cell, which can complicate production and significantly increase costs;
3. administration of angiogenic growth factors without the further ability to activate phagocytes and thereby enhance efficacy or ameliorate infection or other concomitant disorders;
4. administration of angiogenic growth factors without the further ability to reduce inflammation, thereby reducing deleterious side effects; and
5. administration of a peptide which can stimulate the release of factors that recruit inflammatory cytokines and neutrophils to the site of a wound, causing pain and inflammation.

Therefore, in light of the available treatments for promoting wound healing by stimulating angiogenesis, there is a need to provide practical, cost-effective therapies that enhance or optimize chronic wound healing without causing deleterious side effects.

SUMMARY OF THE INVENTION

The present invention provides novel therapeutic peptides, and methods for their use to modulate endogenous cytokine expression in a subject, promote angiogenesis and/or modulate a subject's immune system. The therapeutic peptide consists of only 5 to 6 amino acids, and is selected from the group consisting of:

X1-Q-X2-X3-X4-X5; and

X1-N-S-X3-X4-X5 wherein X1 is selected from the group consisting of N, V, W, and Y;

X2 is selected from the group consisting of H, A, and P;

X3 is selected from the group consisting of T, Q, and S;

X4 is selected from the group consisting of P, Q, H, L, and Y; and

X5 is selected from the group consisting of R and S, or is absent.

Preferred peptides include for example, WNSTL (SEQ ID NO:1), NQHTPR (SEQ ID NO:2), WNSTY (SEQ ID NO:5), YNSTL (SEQ ID NO:6), YQPSL (SEQ ID NO:7), VQATQS (SEQ ID NO:8), and [VNSQH] *VSNQH* (SEQ ID NO:9). Preferably, the peptide is in substantially pure form. Typically it is desired that the peptide be at least 80% pure by weight. In one embodiment the N-terminus may also be acetylated for stability. It is also preferable that the peptide is pro-angiogenic. In a preferred embodiment, the peptides of the invention comprise a peptide construct with at least two or more arms. The construct typically has a central framework and each arm consists of a core sequence linked to the central framework via a linker. Each core sequence of the peptide construct can be the same or different. In a preferred embodiment, the core sequence is the same for each arm of peptide construct. Furthermore, the core sequence is preferably selected from the group of therapeutic peptides described above.

The present invention also provides therapeutic compositions comprising at least one peptide of the invention and a pharmaceutically acceptable carrier.

In yet another aspect of the invention, the invention provides a method of modulating the cytokine expression in a subject. The method preferably comprises administering to a subject one or more peptides of the invention in an amount sufficient to increase the expression of at least one beneficial endogenous cytokine and/or reducing expression of at least one harmful cytokine.

The peptides of the invention can be specifically used to treat certain diseases, and especially induce angiogenesis and wound healing in a subject. In certain embodiments, the peptide is administered in amount sufficient to stimulate angiogenesis in a subject with a wound.

BRIEF DESCRIPTION OF THE DRAWINGS

FIG. 1 illustrates a molecular structure of one embodiment of the present invention, a multivalent peptide construct containing four peptides according to the invention, each of which is linked to a central core structure via a linker sequence;

FIG. 2A illustrates the chemical structure of a peptide construct according to one embodiment of the present invention, the construct contains four copies of the core sequence WNSTL (SEQ ID NO:1) linked to a branched central framework structure;

FIG. 2B illustrates the chemical structure of a peptide construct according to one embodiment of the present invention, the construct contains four copies of the core sequence NQHTPR (SEQ ID NO:2) linked to a branched central framework;

FIG. 3 illustrates the structure of a reporter tag that can be added to a peptide according to the present invention, a C-terminal extension containing a fluorescent dansyl group; and FIG. 4 is a bar graph of data illustrating the stimulation of growth of a tumor as the result of pro-angiogenic activity by one embodiment of the present invention, the quadravalent peptide construct containing the core sequence WNSTL (SEQ ID NO:1) as illustrated in FIG. 2A.

DETAILED DESCRIPTION OF THE PREFERRED EMBODIMENTS

To provide a therapeutic agent with broad properties that stimulate angiogenesis, a process essential to wound healing and restoration of circulation to damaged tissues, the agent should enhance healing without inducing clinically deleterious side effects such as inflammation, and preferably would act in concert with phagocytic activity to eliminate tissue debris and attenuate bacterial infections. The peptides of the present invention meet these goals by concomitantly inducing release of beneficial cytokines, inhibiting the release of deleterious cytokines and stimulating the activity of phagocytic cells. Treatment with the peptides of the present invention induces the healing process by providing a sustained endogenous elevation of an array of beneficial cytokines, in contrast to the administration of a single exogenous cytokine.

In the following description, and for the purposes of explanation, numerous specific details are set forth in order to provide a thorough understanding of the various aspects of the invention. It will be understood, however, by those skilled in the art, that the structures, compositions, and methods are sometimes shown or discussed generally in order to avoid obscuring the invention. In many cases, a description of the material and operation is sufficient to enable one to implement the various forms of the invention.

It should be noted that there are many different and alternative technologies and treatments to which the disclosed inventions may be applied, and the full scope of the inventions is not limited to the examples that are described below. Unless otherwise defined, all technical and scientific terms used herein have the same meaning as commonly understood by one of ordinary skill in the art to which this invention belongs.

The present invention comprises therapeutic angiogenic peptides, compositions of those peptides for administration to a subject in need, and methods to stimulate both angiogenesis and the immune system of a subject through the administration of compositions containing those peptides.

The single letter designation for amino acids is used predominately herein. As is well known by one of skill in the art, the single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; Y is tyrosine.

The Inventors have identified a series of polypeptides that modulate the release of specific cytokines and/or stimulate the immune response. These polypeptides may be particularly beneficial to stimulate wound healing in an injured subject. In general, the advantage of this invention is the modulated release of specific cytokines and the stimulation of angiogenesis. Nonlimiting examples of cytokines include immunoregulatory proteins such as interleukins and interferons, which are secreted by cells of the immune system and can affect the immune response. More particularly, the present invention relates to a family of synthetic peptides capable of inducing the release of beneficial cytokines which can therapeutically stimulate wound healing without inducing deleterious side effects.

Thus, in a first aspect, the present invention provides a therapeutic peptide consisting of 5 to 6 amino acids in length. The therapeutic peptide modulates cytokine expression and preferably is angiogenic. Advantageously, the therapeutic peptide may be reacted with acetic anhydride as well as other compounds to acetylate the N-terminus of the therapeutic peptide. This acetylation stabilizes the peptide and therefore is preferred.

The therapeutic peptides are preferably in a substantially purified form. As used herein, the term "substantially purified" refers to material which is substantially or essentially free from components which normally accompany it as found in its native state. When the material is synthesized, the material is substantially or essentially free of cellular material, gel materials, culture medium, chemical precursors, contaminating polypeptides, nucleic acids, and other chemicals. Generally, the isolated or synthesized peptide will comprise more than 70% or 80% (dry weight) of all macromolecular species present in the preparation. Preferably, the protein is purified to represent greater than 90% (dry weight) of all macromolecular species present. More preferably the protein is purified to greater than 95% (dry weight), and most preferably the protein is purified to essential homogeneity, wherein other macromolecular species are not detected by conventional techniques.

Preferred therapeutic peptides for this first aspect of the invention are selected from the group consisting of:

X1×2×3×4×5×6 wherein X1 is selected from the group consisting of N, V, W, and Y, or is absent;

X2 is selected from the group consisting of Q, V, S, W, N, and Y;

X3 is selected from the group consisting of H, A, S, N, Q, and P;

X4 is selected from the group consisting of T, N, Q, S, and P;

X5 is selected from the group consisting of P, Q, H, T, L, Y, S; and

X6 is selected from the group consisting of R, S, H, L, Y, or is absent.

More preferably,

X1 is selected from the group consisting of N, V, W, and Y;

X2 is selected from the group consisting of Q, S, and N;

X3 is selected from the group consisting of H, A, N, S, and P;

X4 is selected from the group consisting of T, Q, and S;

X5 is selected from the group consisting of P, Q, H, L, and Y; and

X6 is selected from the group consisting of R and S, or is absent.

And still more preferably,

X1 is selected from the group consisting of V, W, and Y;

X2 is selected from the group consisting of Q, S, and N;

X3 is selected from the group consisting of N, S, and P;

X4 is selected from the group consisting of T, Q, and S;

X5 is selected from the group consisting of H, L, and Y; and

X6 is absent.

In an alternative preferred embodiment, the therapeutic peptide is selected from the group consisting of:

X1-Q-X2-X3-X4-X5; and

X1-N-S-X3-X4-X5 wherein X1 is selected from the group consisting of N, V, W, and Y;

X2 is selected from the group consisting of H, A, and P;

X3 is selected from the group consisting of T, Q, and S;

X4 is selected from the group consisting of P, Q, H, L, and Y; and

X5 is selected from the group consisting of R and S, or is absent.

More preferably,

X1 is selected from the group consisting of V, W, and Y;

X2 is selected from the group consisting of A and P;

X3 is selected from the group consisting of T and S;

X4 is selected from the group consisting of Q and Y;

X5 is S or absent.

Still more preferably,

X1 is selected from the group consisting of W and V;

X2 is A;

X3 is T;

X4 is selected from the group consisting of L and Y;

X5 is S or absent.

In a most preferred embodiment, the therapeutic peptide is selected from the group consisting of WNSTL (SEQ ID NO:1), NQHTPR (SEQ ID NO:2), WNSTY (SEQ ID NO:5), YNSTL (SEQ ID NO:6), YQPSL (SEQ ID NO:7), VQATQS (SEQ ID NO:8), and [VNSQH] *VSNQH* (SEQ ID NO:9).

In a second aspect, the present invention provides a therapeutic angiogenic peptide comprising a construct and at least two arms. The construct has a central framework and each arm consists of a core sequence linked to the central framework via a linker. Each core sequence can be the same or different.

As used herein, "construct" is defined as the entire molecule and comprises the central framework linked with at least two arms. In a preferred embodiment, the construct comprises the central framework linked to 2 or more arms, e.g., 3, 4, 5, 6, 7, 8, 9, 10, 11, or 12 arms, preferably 2 to 8 arms. In a further preferred embodiment, the construct comprises the central framework linked to 4 arms. Each arm within the construct may consist of the same or different core sequence and/or linker. In one preferred embodiment, the core sequence is the same between arms.

The "central framework" is defined as the structural core of the construct, providing a structure for attaching the arms to a central structure. The central framework is based on a core molecule which has at least two functional groups to which molecular branches having terminal functional groups are bonded, e.g., a tri-lysine to which the peptide arms. Such molecules may be developed or created to present a varying number of branches, depending on the number of monomers branched from the core molecule. Each non-terminal functional group on each branch provides a means of attachment to an arm. Non-limiting examples of preferred central framework include: ethylenediamine (1,2-ethanediamine), ethylene glycol (1,2-dihydroxyethane), polyols such as glycerol, 3,5-diaminobenzoic acid, 1,3,5-triaminobenzene, and monocarboxylic-diamino compounds of intermediate length. Preferably, the monocarboxylic-diamino compounds are within the range of 2 to 10 carbons in length. Non-limiting examples of such compounds are 2,3-diaminopropionic acid and 2,6-diaminocaproic acid. In a more preferred embodiment, the monocarboxylic-diamino compound is 6 carbons in length. Compounds that provide an aromatic central framework which absorbs light may be beneficial for determining peptide concentration as well. The carboxyl group of the monocarboxylic-diamino compounds allows the addition of C-terminal tags including biotin derivatives. In a preferred embodiment, the central framework comprises a tri-lysine core (a lysine residue as the core molecule bonded to two lysine residues, each through its carboxyl group, to one of the amino groups of the central lysine residue), providing a central frame work for up to four arms.

The "arm" is defined as the core sequence, defined below, plus the linker. The "linker" is defined as a peptide chain or other molecule that connects the central framework to the core sequence. In a preferred embodiment, the linker comprises, but is not limited to, certain linker peptide sequences, polyethylene glycol, 6-aminocaproic acid (6-aminohexanoic acid), 8-aminooctanoic acid, and dextran. In a most preferred embodiment, the linker is GGGS (SEQ ID NO:3), GGGSGGGS (SEQ ID NO:4), SSSS (SEQ ID NO:10), SSSSSSSS (SEQ ID NO:11), or variations thereof. The length of the linker can be adjusted, for example, the linker GGGS (SEQ ID NO:3) can be repeated to provide variable lengths, e.g., repeated twice (GGGSGGGS (SEQ ID NO:4)), or even three or more times; additional serine residues could be added to SSSS (SEQ ID NO:10) to also produce varying lengths of the linker.

The "core sequence" is defined as the functional portion of each arm that provides the therapeutic effect. The core sequence is preferably selected from the group of therapeutic peptides of 5 to 6 amino acids in length described above in the first aspect. In a most preferred embodiment, the core sequence is selected from the group consisting specifically of: WNSTL (SEQ ID NO:1), NQHTPR (SEQ ID NO:2), WNSTY (SEQ ID NO:5), YNSTL (SEQ ID NO:6), YQPSL (SEQ ID NO:7), VQATQS (SEQ ID NO:8), and [VNSQH] *VSNQH* (SEQ ID NO:9).

A specific illustration of a therapeutic peptide of the invention is set forth in FIG. 1. In FIG. 1, the therapeutic peptide is in the form of a multivalent immuno-regulatory peptide construct 10. The construct 10 can be synthesized with at least two arms 1, (e.g., two, three, four, eight or more arms 1). The same core peptide sequence 2 can be used for each arm or, alternatively, two or more different core peptide sequences 2 can be used for each arm 1 instead. The length of the linker 3 between the central framework 4 of the construct 10 and the core peptide sequence 2 determines the length of each of the arms 1. The arms 1 illustrated in FIG. 1, for example, are often about 3±0.5 nm in length depending on conformation, or approximately 7±0.5 nm across the molecule. Cell-surface domains of known receptor proteins are correspondingly about 3 to 4 nm in diameter. This distance can be adjusted by increasing or decreasing the length of the linker 3. Preferably, the length of each of the linkers 3 allows for and promotes cross-linking with receptors. The multidimensional nature of the structure illustrated in FIG. 1 was obtained using standard molecular modeling techniques.

In a third aspect, the present invention provides a therapeutic composition, preferably pro-angiogenic. The composition preferably comprises one or more of the therapeutic peptides disclosed herein, and a pharmaceutically acceptable carrier. As used herein the term "pharmaceutically acceptable" means approved by a regulatory agency of the Federal or state government or listed in the U.S. Pharmacopeia or other generally recognized pharmacopeia for use in animals, and more particularly in humans. There term "carrier" refers to a diluent, adjuvant, excipient, or vehicle with which an active ingredient is administered. Such pharmaceutical carriers can be liquids, such as water and oils, including those of petroleum, animal, vegetable or synthetic origin. Preferably, the pharmaceutically acceptable carrier comprises, but is not limited to, a saline solution, a polyether, and/or water. Examples of suitable carriers, include water, phosphate-buffered saline, sodium chloride solutions, polyethylene-glycol solutions, etc. The type and amount of carrier is typically influenced by the route of administration. For example, when the peptides are administered via injection, preferable carriers comprise, but are not limited to, a phosphate-buffered saline solution having a pH between 6.5 and 7.5 (e.g., about 7.2) or a sodium chloride solution (e.g., 100-150 mM); whereas when administered via a patch, the carrier preferably selected from the group consisting of: polyethyleneglycol solution (e.g., 250 mg/mL of PEG8000), carbopol gel base, propylene glycol, methyl paraben, ethyl paraben, HPMC gel base (hydroxypropylmethyl cellulose), PEG 4000, PEG 300, DMSO, isopropyl myristate, mineral oil, white petrolatum, bees wax, glycerine and water.

In a fourth aspect, the present invention provides a method for modulating the cytokine expression in a subject. Being able to modulate the expression of endogenous cytokines provides a means of regulating and treating a significant number of diseases. The method comprises the steps of administering to the subject one or more of the therapeutic peptides described herein, wherein the peptide is administered in an amount sufficient to increase or decrease the expression of at least one endogenous cytokine in the subject. Preferably, the subject being treated by the method is an animal, more preferably a mammal, e.g., monkey, dog, cat, horse, cow, sheep, pig, and most preferably the subject is human.

In a preferred embodiment, the peptide modulates the expression of at least one cytokine selected from the group consisting of: Eotaxin, Eotaxin-2, ICAM-1, 1-309, IL-4, IL-8, IL-10, IL-11, IL-15, IL-16, IL-17, IL-21, RANTES, sTNF RI, sTNF RII, IL-12p40, IL-12p70, M-CSF, MCP-2, MIG, PDGF-BB, TNF-β, MIP-1b, GCSF, and TIMP-2. More specifically, preferably the peptides increase the endogenous expression of at least one cytokine selected from the group consisting of: IL-11, IL-12p40, IL-12p70, RANTES, sTNF RI, PDGF-BB, Eotaxin, Eotaxin-2, IL-15, IL-16, IL-17, MCP-2, M-CSF, MIG, TNF-β, sTNF RII, TIMP-2. Most preferably, the peptide increases at least two, three, four, or more of these cytokines. Moreover, expression of these cytokines is preferably increased by at least 20%, more preferably 50%, and most preferably 80%. Sometimes the beneficial endogenous cytokine is increased by even more than 100%.

In addition, preferably the peptide decreases the endogenous expression of at least one cytokine selected from the group consisting of: IL-7, IL-8, Ecotaxin-2, GCSF, ICAM-1, INF-γ, IL-6SR, TIMP-2, MCP-1, and MIP-1b. Likewise, expression of these cytokines is preferably decreased by at least 20%, more preferably 50%, and most preferably 80%. Sometimes the beneficial endogenous cytokine is decreased by even more than 100%.

In a further preferred embodiment, the peptide stimulates the release of those cytokines that induce angiogenesis. In another preferred embodiment, the peptide does not stimulate the release of those cytokines that cause or exacerbate inflammation. In a specific embodiment, the peptide decreases at least one cytokine selected from the group consisting of: IL-1a, IL-8, IL-13, IL-11, IL-12p40, and IL-12p70. It is most preferable that the peptide does not stimulate the release of IL-8. In this context, "does not stimulate" means levels of IL-10 are not statistically greater (preferably $p>0.20$; more preferably $p>0.10$; and most preferably $p>0.05$) between treatments and control samples when examined in experiments similar to those described in Example 3.

Preferably the "amount sufficient" as used herein, is the amount necessary to modulate cytokine expression in a subject. In a more specific embodiment, the amount sufficient is an amount within the range of 1 pmole to 1 nmole per g of body weight and/or within the range of 0.1 to 300 mg per dose. For a typical adult human, the amount sufficient is usually within the range of 1 to 100 mg, more preferably, 1 to 70 mg, and most preferably 1 to 50 mg per dose. Based on the subject's body weight, preferably the amount is 0.01 to 1.4 mg/kg; more preferably 0.01 to 1 mg/kg; and most preferably between 0.01 to 0.7 mg/kg of the subject's body weight per dose. As a nonlimiting example, an amount sufficient to treat the disease in a typical 70 kg adult human would be 0.1 mg/kg of the subject's body weight, 2 μmole, or 7 mg per dose. As would be known to one skilled in the art, the lifetime of activated macrophages suggests that a dose should be administered once about every 2 to 6 days, more preferably 1 or 2 times a week, until the disease is treated, resulting in an improvement of at least one symptom, and preferably by eradication from the body of the subject.

In a fifth aspect, the present invention provides a method for stimulating wound healing via induction of angiogenesis in a subject. The method comprises the steps of administering to the subject a composition comprising a peptide of the invention, wherein the peptide is in an amount sufficient to stimulate angiogenesis in an area substantially near a subject's wound. An area substantially near a subject's wound" refers to the area of the body, preferably within 6 inches, more preferably within 4 inches, and most preferably within 2 inches from the outer edge of the wound being treated. Preferably, the subject being treated by the method is an animal, more preferably a mammal, and most preferably a human.

Administration of the composition to the subject comprises transferring the composition into the body of the subject in an amount sufficient to stimulate wound healing via induction of angiogenesis. The composition of the invention can be administered via any suitable route that achieves the intended purpose. For example, administration can be by subcutaneous, intravenous, intramuscular, intraperitoneal, buccal, or ocular routes, rectally, parenterally, intrasystemically, topically (as by powders, ointments, drops or transdermal patch), or as an oral or nasal spray. Alternatively, or concurrently, administration can be by the oral route. The dosage administered will be dependent upon the age, health, and weight of the recipient, kind of concurrent treatment, if any, frequency of treatment, and the nature of the effect desired.

In a preferred embodiment, the composition is administered orally. In this embodiment, the composition is in an edible form, including for example, powders, granules, capsules, pills, tablets, elixirs, suspensions, emulsions, syrups and the like. These preparations may be subjected to modification such as sustained-release, stabilization, easy disintegration, poor disintegration, enteric coating, easy absorption and the like. Preferably in this embodiment, the composition is in a form that allows for passage through the stomach and release in the intestine for absorption in intestinal lumen, e.g., enteric coated formations based on pH or timed release. Additionally, the dosage may be in the form of chewable preparations, sublingual preparations, buccal preparations, troches, ointments, patches, solutions and the like. These preparations may be also subjected to modification such as sustained-release, stabilization, easy disintegration, poor disintegration, enteric coating, easy absorption and the like.

In another embodiment, the composition is administered via injection, e.g., subcutaneous, intramuscular, intravenous, and intraperitoneal injection, preferably subcutaneously. When the composition is formulated for transdermal administration, the composition preferably comprises PEG8000, but may be comprised of other suitable carriers such as carbopol gel base, propylene glycol, methyl paraben, ethyl paraben, HPMC gel base, PEG 4000, PEG 300, DMSO, isopropyl myristate, mineral oil, white petrolatum, bees wax, glycerine and water in a medical patch. The patch preferably comprises 1 to 8 mg, more preferably 2 to 6 mg, and most preferably about 4 mg of therapeutic peptides per mL of solution in the patch. A patch typically comprises 1 to 75 mL, and more preferably 1 to 18 mL of solution within the patch. When administering to the subject, the patch should be in contact with the subject's skin for a period of at least 2 to 72 hours. A typical patch would be in contact with the subject's skin for approximately 24 to 48 hours.

As would be known by one skilled in the art, the PDGF class of cytokines is instrumental in the process of angiogenesis. Thus, in a preferred embodiment, the stimulation of wound healing via the induction of angiogenesis increases the production of cytokines comprising but not limited to the PDGF class. In a further preferred embodiment, the administration of the composition stimulates the production of the cytokine PDGF-BB. "Stimulates the production" in this instance means PDGF-BB production is preferably increased by at least 20%, more preferably 50%, and most preferably 80%. Data from TABLE 3 suggests PDGF-BB production may increase by at least 90%.

Preferably the administration of the compositions of the invention does not cause inflammation in the subject. As would be known by one skilled in the art, inflammation in response to a wound is often caused by the release of the cytokines IL-8 and ICAM-1 in the body. Thus, in a further preferred embodiment, the administration of the composition inhibits the production of cytokines that cause inflammation or at least does not increase the production of these cytokines. More preferably, the administration of the composition inhibits the production of IL-8. In certain embodiment, the composition actually promotes the release and/or production of anti-inflammatory cytokines.

As would be known by one skilled in the art, selective cross-linking of cell-surface receptors by a multivalent structure incorporating at least one peptide embodiment of the present invention may attenuate bacterial infections by stimulating activity of phagocytic cells that are recruited to the injured or infected tissue. Phagocytic cells respond to the presence of bacterial cells containing lipopolysaccharide (LPS) on their surface by engulfing the cells into phagocytic vacuoles and digesting the bacterial cells. In addition, the phagocytic cells respond to the presence of antibodies directed toward—and bound to—a pathogen such as a bacterial cell, fungal cell or virus. Thus, in another preferred embodiment, the administration of the composition enhances the ability of the subject's immune system to ward off or attenuate infection. In a most preferred embodiment, the infection is attenuated or prevented at or substantially near the target wound area. An area substantially near a subject's wound" refers to the area of the body, preferably within 6 inches, more preferably within 4 inches, and most preferably within 2 inches from the outer edge of the wound being treated.

EXAMPLES

Elements and acts in the examples are intended to illustrate the invention for the sake of simplicity and have not necessarily been rendered according to any particular sequence or embodiment. The examples are further intended to establish possession of the invention by the Inventors.

Example 1

Peptide Design and Synthesis

A screen of peptide sequences identified one set of sequences of interest. The corresponding peptides were synthesized by solid-phase methods using standard Fmoc side chain protection. Branched peptides were constructed on a central tri-lysine framework, which allows four identical sequences within the same structure. A $(Gly)_3$-Ser (GGGS, SEQ ID NO:3) linker sequence was included to distance the active sequence from the central framework. Distances between the active sequences can be adjusted by decreasing or increasing the length of the linker, including without limitation the use of two linkers in tandem (GGGSGGGS, SEQ ID NO:4) or by inserting any inert linker such as polyethylene glycol (PEG) of a variable length. The branched structure was designed to have enhanced activity by causing receptor clustering (cross-linking) on the surface of responsive cells.

The peptides were synthesized on PAL-PEG-polystyrene resin (Applied Biosystems, Foster City, Calif.) utilizing Fmoc (9-fluorenylmethoxycarbonyl)-protected amino acids and a Milligen Biosearch 9050+ continuous flow peptide synthesizer (Millipore Corporation, Billerica, Mass.).

The C-terminus of the central framework is typically a lysine residue containing an amide derivative of the carboxyl group. However, the C-terminus can be modified to include additional C-terminal amino acids such as a cysteine residue, to which tags such as fluorescent groups can be added, or an ϵ-biotinyl-N-lysine (biotinyl-K) residue useful for subsequent purification processes. In addition, an amino acid such as β-alanine (βA) or tryptophan can be inserted between the added C-terminal amino acid and the C-terminal lysine residue of the central framework in order to provide a spacer or a means to determine concentration by absorbance. Non-limiting examples of such modified C-terminal lysine residues on the central framework include K-βA-C and K-W-biotinyl-K, respectively. Furthermore, additional lysine residues can be added to either one or both of the α- and ϵ-amino groups of a modified C-terminal lysine on the central framework to yield, for example, $(K)_2K$, $(K)_2K$-βA-C or $(K)_2K$-W-biotinyl-K, thereby forming branched structures in which the α- and ϵ-amino groups are available for extension.

The lysine residues used at the branch points are incorporated with Fmoc protection on both the α- and ϵ-amino groups, so that both become available for amide bond formation after the standard deprotection reaction with piperidine. A dansyl group (or other fluorescent tag) may be incorporated by reaction with the thiol group on the C-terminal cysteine residue using 5-((((2 iodoacetyl)amino)ethyl)amino)naphthalene-1-sulfonic acid (1,5-IAEDANS) following a standard protocol for thiol-reactive probes (Invitrogen Corp., Carlsbad, Calif.). Biotin is attached to lysine through an amide linkage to the side chain amino group which, because of its high affinity with streptavidin, provides a means to retrieve the peptide with associated proteins from reaction mixtures in order to study the interaction of the peptide with cellular components.

The peptides were built attached to a solid-phase resin, which was chosen such that when the peptide is cleaved from the resin, the carboxyl group at the C-terminus of the peptide is released as the amide. Each of the four amino groups of the tri-lysine central framework was extended by addition of the linker, GGGS (SEQ ID NO:3), followed by the core sequence.

After cleavage from the resin bed, the product can be substantially or completely purified by HPLC on a preparative Jupiter Proteo C12 column (21.2 mm×250 mm) (Phenomenex, Inc., Torrance, Calif.) using a gradient from 8% to 18% acetonitrile in water containing 10 mM trifluoroacetic acid (TFA). The purity of the final peptide product was confirmed by mass spectroscopy performed using a Voyager DE STR mass spectrometer (Applied Biosystems, Foster City, Calif.). HPLC-purified peptide was dried under vacuum, dissolved in sterile phosphate buffered saline, pH 7.2 (PBS) and passed through a gel filtration column of Sephadex G 15 or G 25 (1×48 cm for small samples) to separate TFA from the peptide. The column is then eluted with sterile PBS. Endotoxin is removed by passage of the peptide through a DEAE-Sephadex A-25 column.

Alternatively, the product is purified by use of a C18 reverse-phase cartridge, ion exchange chromatography, and gel filtration chromatography to remove side products of synthesis. Concentration can be determined by absorbance of the fluorophore (e.g., dansyl group, extinction coefficient, $\epsilon_{mM}$=5.7 $cm^{-1}$ at 336 nm), absorbance of the peptide bond at 210 nm ($\epsilon_{mg/mL}$≈31 $cm^{-1}$), absorbance of aromatic amino acids (e.g., tryptophan, $\epsilon_{mM}$=5.6 $cm^{-1}$ at 280 nm) in the peptide (when present) and/or absorbance of the bicinchoninic acid reagent (Pierce Biotechnology, Rockford, Ill.). The peptide solutions can be adjusted to the desired concentration and filter-sterilized prior to use.

Example 2

Core Peptide Sequences: WNSTL (SEQ ID NO:1) and NQHTPR (SEQ ID NO:2)

The peptides (WNSTL, SEQ ID NO:1) and (NQHTPR, SEQ ID NO:2) were identified through a screen of peptide sequences as potentially of interest. The sequences were synthesized on a tri-lysine core according to Posnett et al., J. Biol. Chem., 263: 1719-25, 1988, with a linker (GGGS, SEQ ID NO:3) included with the sequence to extend the active peptide away from the core.

FIGS. 2A-B illustrate the chemical structure of these two embodiments of the invention. In these embodiments, R═H or can be an adduct containing a fluorescent tag such as the dansyl group shown in FIG. 3. The peptide constructs illustrated contain four identical sequences, each of which is connected to a branched central tri-lysine framework via a $(Gly)_3$Ser (GGGS, SEQ ID NO:3) linker. FIG. 2A is a branched peptide construct according to one embodiment of the invention, a peptide construct which contains four copies of the core sequence WNSTL (SEQ ID NO:1). The peptide embodiment containing R═H has a molecular mass of 3,841.16 Daltons.

FIG. 2B illustrates the structure of the construct containing four copies of the N-terminal core sequence NQHTPR (SEQ ID NO:2). This peptide embodiment containing R═H has a molecular mass of 4,543.89. In another embodiment, a C-terminal extension containing β-alanine, cysteine and a dansyl tag, as shown in FIG. 3, is covalently added to the construct illustrated in FIG. 2B, resulting in a peptide having a molecular mass of 4,850.23 Daltons.

Example 3

Regulation of Cytokine Release

To determine whether the peptides regulate induction or inhibition of release of cytokines, cultured peripheral blood mononuclear cells (PBMCs) were treated with one peptide embodiment of the invention and, after 4 hour incubation, the medium was collected and assayed for changes in the amounts of 40 different cytokines. The peptide construct containing four copies of WNSTL (SEQ ID NO:1), illustrated in FIG. 2A, was added at a concentration of 100 nM in each of the assays. The PBMC cultures were established with cells from Cellular Technology, Ltd. (Shaker Heights, Ohio). Approximately 3 million cells of frozen human PBMCs were thawed at 37° C. and transferred to a 50 mL conical tube where 8 mL of wash medium were added slowly. Then an additional 8 mL were added and swirled to mix. The cells were then centrifuged at 330 g for 10 min, the supernatant was removed and the pellet was resuspended in 10 mL wash medium and centrifuged as above. The washed cells were then resuspended in RPMI 1640 medium containing 10% FBS to about 6 million cells per mL and 100 μL of the suspension were added into each well of a 96-well microtiter plate and incubated overnight at 37° C. in humidified 5% $CO_2$. After 24 hr, the medium was replaced with 200 μL fresh RPMI 1640 medium containing 10% FBS and incubated at 37° C. in humidified 5% $CO_2$ for 2 days. For the data shown in TABLE 1, an aliquot of the peptide construct was added to samples in duplicate at a final concentration of 5 nM or 100 nM and incubated at 37° C. in humidified 5% $CO_2$ for 4 hr. For other experiments (data not included), the incubation was continued for 24 hr. The medium was then removed and stored at 80° C. The samples were analyzed for production of cytokines. One set of control cells was not treated with an experimental agent. A second set of control cells was treated with LPS, the agent commonly used to induce production of a variety of inflammatory cytokines. The positive control for inflammation provided by this second set of control cells was essential to ensure that the peptides do not produce an unregulated inflammatory response.

Assays of cytokine levels in samples of culture media were performed using methods developed by RayBiotech, Inc. (Norcross, Ga.). In this technology, membrane arrays of antibodies against cytokines were incubated with samples of media. After washing, the array was incubated with a cocktail of all antibodies tagged with biotin. The membrane was then washed free of unbound antibodies and incubated with streptavidin labeled with a fluorescent dye. After a final wash, the membrane arrays were read in a fluorescence detector and the intensities of the spots quantitated to obtain relative values.

TABLES 1-3 list a number of cytokines whose concentrations in a medium of PBMC cultures can be altered as the result of treatment of the cells with peptide embodiments of the present invention. The cytokines thus affected include without limitation:

Eotaxin (chemoattractant, induces substantial accumulation of eosinophils);

Eotaxin-2 (induces chemotaxis of eosinophils and basophils, release of histamine);

GCSF (granulocyte colony stimulating factor, growth factor);

ICAM-1 (intercellular adhesion molecule-1, binds to integrins, human rhinovirus receptor);

IL-1β (Interleukin 1β, a mediator of inflammatory reactions);

IL-4 (promotes proliferation and differentiation of B-cells and inhibits production of inflammatory cytokines such as IL-1, IL-6 and TNF-α);

IL-6SR (soluble receptor for IL-6);

IL-7 (stimulates proliferation of precursor B and T cells);

IL-8 (chemoattractant and activator of neutrophils);

IL-10 (inhibits synthesis of inflammatory cytokines such as INF-γ, IL-2 and TNF-β);

IL-11 (induces inflammatory responses, promotes immune responses);

IL-12 (contains subunits of 40 and 70 kDa, activates NK-cells and stimulates proliferation of lymphoblasts);

IL-15 (has many of the same properties as IL-2, may contribute to T-cell mediated immune responses);

IL-16 (chemoattractant and activator for cells that express CD4);

IL-17 (functions as a mediator of angiogenesis that stimulates migration of vascular endothelial cells and cord formation and regulates production of a variety of growth factors promoting angiogenesis);

INF-γ (Interferon-gamma, has antiviral, immunoregulatory and anti-tumor properties);

MCP-1,2 (monocyte chemotactic proteins);

M-CSF (induces proliferation and stimulates monocytes and macrophages); MIG (chemoattractant for stimulated T cells but not active on neutrophils or monocytes);

MIP-1b (macrophage inflammatory protein, involved in cell activation of granulocytes and killer cells);

PDGF-BB (platelet-derived growth factor, BB homodimer);

RANTES (regulated on activation, normal T cell expressed, and secreted; chemotactic for T cells);

sTNF RI, Rh (soluble forms of receptor RI or RII for tumor necrosis factor (TNF));

TIMP-2 (tissue inhibitor of metalloproteinases of the extracellular matrix); and TNF-β (promotes the proliferation of fibroblasts and is involved in wound healing).

TABLE 1 contains data showing cytokines that are released at a significantly higher or lower rate (compared to untreated controls) during a 4-hour incubation of PBMCs with the branched peptide construct containing four copies of WNSTL (SEQ ID NO:1) in the presence of serum. One set of control samples was not treated with peptide and a second set of control samples was treated with lipopolysaccharide (LPS) in the absence of the peptide construct. The structure of the construct is illustrated in FIG. 2A. Among the cytokines that are induced to more than two-fold higher concentrations as a result of incubation with the construct containing four copies of WNSTL (SEQ ID NO:1) are PDGF-BB, IL-1β, IL-4, IL-1, IL-12 and RANTES. In contrast, several cytokines show more than a two-fold decrease in concentration as compared to untreated control samples with this peptide. The decrease in IL-8 concentration in the peptide-treated sample, as compared with the amount of IL-8 in the sample treated with the proto-typical inflammatory agent LPS, is particularly notable. Furthermore, when compared to untreated control samples, the peptides did not induce a change in the amount of the inflammatory cytokine IL-6. However, IL-6 levels were significantly elevated in samples treated with LPS in the absence of peptide. In one experiment, for example, the peptide treated sample had a relative IL-6 concentration of 93, the untreated control sample, 98, and the LPS-treated sample (in the absence of peptide), 5,879. Because the concentration of IL-6 in the peptide treated sample was not significantly different from the untreated control sample, the data for IL-6 are not included in TABLES 1 or 2. The increase in the pro-angiogenic PDGF-BB and the decrease in the inflammatory IL-8, without concomitant stimulation of inflammation, are of particular importance with respect to wound healing.

TABLE 1

Relative Cytokine Concentration after Incubation of PBMCs in Serum with a Peptide Construct Containing Four Copies of the Core Sequence WNSTL (SEQ ID NO: 1).

| Cytokine | WNSTL (SEQ ID NO: 1) | Untreated (control) | LPS (control) |
|---|---|---|---|
| | | Increased: | |
| PDGF-BB | 159 | 43 | 56 |
| IL-1β | 120 | 44 | 47 |
| IL-4 | 97 | 30 | 49 |
| IL-11 | 49 | 17 | 26 |
| IL-12p40 | 228 | 108 | 46 |
| IL-12p70 | 131 | 90 | 89 |
| RANTES | 145 | 80 | 114 |
| STNF RI | 78 | 42 | 58 |
| | | Decreased: | |
| IL-7 | 93 | 154 | 178 |
| IL-8 | 144 | 417 | 840 |
| IL-10 | 43 | 101 | 218 |
| Eotaxin-2 | 109 | 1934 | 469 |
| GCSF | 50 | 108 | 120 |
| ICAM-1 | 44 | 57 | 53 |
| INF-γ | 103 | 134 | 158 |
| IL-6sR | 32 | 52 | 52 |
| TIMP-2 | 25 | 58 | 92 |
| MCP-1 | 968 | 1464 | 1844 |

Relative cytokine concentration data for the peptide construct containing four copies of the core sequence NQHTPR (SEQ ID NO:2) is similarly outlined in TABLE 2. The structure of the construct is illustrated in FIG. 2B. Cytokines were again observed at significantly higher or lower concentrations (relative to controls) after a 4-hour incubation with the branched construct containing four copies of the core sequence NQHTPR (SEQ ID NO:2). The data in TABLE 2 show that, although the overall pattern of cytokine response to this peptide is somewhat different from that of the quadravalent peptide construct containing the core sequence WNSTL (SEQ ID NO:1) shown in TABLE 1, it similarly induces a higher amount of PDGF and a lower amount of IL-8.

TABLE 2

Relative Cytokine Concentration after Incubation of PBMCs in Serum with the Peptide Construct Containing Four Copies of the Core Sequence NQHTPR (SEQ ID NO: 2).

| Cytokine | NQHTPR (SEQ ID NO: 2) | Untreated (control) |
|---|---|---|
| | Increased: | |
| PDGF-BB | 84 | 43 |
| Eotaxin | 57 | 32 |
| Eotaxin-2 | 310 | 193 |
| IL-15 | 146 | 97 |
| IL-16 | 8 | 1 |
| IL-17 | 14 | 5 |
| MCP-2 | 90 | 56 |
| M-CSF | 116 | 44 |
| MIG | 100 | 54 |
| TNF-β | 84 | 38 |
| sTNF RII | 26 | 8 |
| TIMP-2 | 110 | 58 |
| | Decreased: | |
| IL-8 | 261 | 417 |
| MIP-1b | 777 | 1172 |

TABLE 3 is based on the same data as TABLES 1-2, and shows the effects of constructs containing four copies of VQATQS (SEQ ID NO:8), VSNQH (SEQ ID NO:9), NQHTPR (SEQ ID:2) and WNSTL (SEQ ID NO:1) on the relative concentrations of cytokines in PBMCs treated for four hours with each peptide construct as compared with untreated control cultures and LPS-treated cells.

TABLE 3

Relative Concentrations of Cytokines in PBMCs Treated for 4 hr with each Peptide Construct as Compared with Untreated Control Cultures and LPS-treated Cells.*

| | Core Sequence of Peptide | | | | Un- | |
|---|---|---|---|---|---|---|
| Cytokine | VQATQS | VSNQH | NQHTPR | WNSTL | treated | LPS |
| Eotaxin | | 47 | 57 | | 32 | 31 |
| Eotaxin-2 | 401 | 470 | 310 | 109 | 193 | 469 |
| GCSF | | | | 50 | 108 | 120 |
| GM-CSF | | 96 | | | 57 | 106 |
| ICAM-1 | | 70 | | 44 | 57 | 53 |
| IFN-γ | | 170 | | 103 | 134 | 158 |
| I-309 | 101 | | | | 26 | 39 |
| IL-1α | | 322 | | | 225 | 246 |
| IL-1β | | | | 120 | 44 | 47 |
| IL-2 | | | | | 86 | 90 |
| IL-3 | | | | | 130 | 132 |
| IL-4 | 64 | | | 97 | 30 | 49 |
| IL-6 | 167 | | | | 98 | 4,375 |
| IL-6sR | | | | 32 | 52 | 52 |
| IL-7 | | | | 93 | 154 | 178 |
| IL-8 | | | 261 | 144 | 417 | 840 |
| IL-10 | 67 | | | 43 | 101 | 218 |
| IL-11 | | | | 49 | 17 | 26 |
| IL-12p40 | 74 | 52 | 45 | 228 | 108 | 46 |
| IL-12p70 | 112 | 117 | 65 | 131 | 90 | 89 |
| IL-13 | | | | | 138 | 125 |
| IL-15 | 134 | 137 | 146 | | 97 | 104 |
| IL-16 | 10 | | 8 | | 1 | 2 |

TABLE 3-continued

Relative Concentrations of Cytokines in PBMCs Treated for 4 hr with each Peptide Construct as Compared with Untreated Control Cultures and LPS-treated Cells.*

| | Core Sequence of Peptide | | | | Un- | |
|---|---|---|---|---|---|---|
| Cytokine | VQATQS | VSNQH | NQHTPR | WNSTL | treated | LPS |
| IL-17 | 21 | 21 | 14 | | 5 | 10 |
| IL-21 | 90 | 130 | 200 | — | 50 | (IFN-γ: 100) |
| IP-10 | 334 | 377 | | | 230 | 268 |
| MCP-1 | 1,966 | | | 968 | 1,464 | 1,844 |
| MCP-2 | | 97 | 90 | | 56 | 177 |
| M-CSF | 90 | | 116 | | 44 | 59 |
| MIG | | 94 | 100 | | 54 | 66 |
| MIP-1a | | | | | 81 | 237 |
| MIP-1b | | | 777 | | 1,172 | 1,828 |
| MIP-1d | | | | | 40 | 38 |
| RANTES | | | | 145 | 80 | 114 |
| TGF-β1 | 83 | | | | 62 | 62 |
| TNF-α | 98 | 138 | | | 73 | 93 |
| TNF-β | 91 | 93 | 84 | | 38 | 95 |
| sTNF RI | 75 | | | 78 | 42 | 58 |
| sTNF RII | 20 | | 26 | | 8 | 26 |
| PDGF-BB | 83 | 82 | 84 | 159 | 43 | 56 |
| TIMP-2 | 175 | 285 | 110 | 25 | 58 | 92 |

*The absence of a number indicates no significant change from untreated control cultures.

Toxicity of the peptide in vivo can be tested by injection of a peptide into animal subjects, including without limitation mice. The peptides can be administered in a number of ways, including without limitation by injection (intravenously, subcutaneously, intramuscularly or intraperitoneally), topically (transmucosally, transbuccally, or transdermally) and/or orally (liquid, tablet or capsule). In preliminary studies on mice, no adverse effects of the peptide on the growth rate of the animals have been observed after injection of an effective dose on alternate days for 1 month (data not shown).

Example 4

Pro-Angiogenic Activity of Peptides

Tumors require vascularization to obtain nutrients to support growth. Therefore, stimulation of growth of a tumor in response to administration of a construct of this invention is an indication of angiogenesis. For this example, a xenograph model system with the nude mouse (nu/nu) was used to determine the effect of peptide on growth of 786-0 human renal cell adenocarcinoma cell line injected into the flank of a mouse so as to induce a tumor. After the tumor was established, peptide was injected subcutaneously on alternate days. The weight of the tumor was estimated by calculation of the volume.

FIG. 4 illustrates data resulting from assays for pro-angiogenic activity for one embodiment of the invention. The bar graph in FIG. 4 shows the average weight of the tumor in mice treated with the peptide construct containing four copies of the core sequence WNSTL (SEQ ID NO:1) at a dose of 0.05 nmole/gm as compared with a control group. The peptide was also assayed in combination with Sorafenib, an anti-angiogenic drug. The results shown in FIG. 4 indicate that growth of the tumor was significantly enhanced, by a factor of 1.7, over the control in mice to which the construct with four copies of the core sequence WNSTL (SEQ ID NO:1) was administered. The drug Sorafenib, an inhibitor of angiogenesis, strongly (but not completely) inhibited the effect of the peptide.

Example 5

Stimulation of Phagocytosis by Peptides

The activity of the peptides to stimulate phagocytosis was assessed by the ability of macrophages to engulf microspheres opsonized with anti-HIV antibodies. A biotin-tagged peptide epitope of a surface protein of HIV-1 was bound to streptavidin on the surface of the beads. An antibody preparation that was raised against this epitope was then bound to the HIV peptide. The beads were then washed and presented to PBMC cultures pretreated with peptides. Macrophages in cultures not treated with peptides had little, if any, phagocytic activity. In multiple control cultures, the number of beads within a macrophage-like cell ranged from 0 to 3. In the cultures treated with peptide constructs containing four copies of the peptide sequences WNSTL (SEQ ID NO:1), NQHTPR (SEQ ID NO:2), or VQATQS (SEQ ID NO:8), an average of 10 beads were counted in each phagocytic cell, with no substantial difference between peptide constructs. These findings suggest a stimulation of phagocytic activity by the peptide constructs compared to untreated cultures. Cultures treated with the cytokine INF-γ exhibited an average of roughly 15 beads per phagocytic cell.

Example 6

Devices or Materials Containing the Peptides

The peptides of the present invention may also be deposited to provide an appropriate coating to a surface, including without limitation bioactive surfaces or inert, non-biological surfaces of a device or materials designed for implantation. The peptides can thus promote healing around the implanted materials in order to achieve vascularization without scarring. They could similarly be used in other in vitro or in vivo applications, including without limitation, with embedded sensors.

The embodiments and examples set forth herein were presented in order to best explain the present invention and its practical application and to thereby enable those of ordinary skill in the art to make and use the invention. Although the examples herein disclose the therapeutic efficacy of the peptides of the present invention with respect to wound healing, for example, the peptides may also be useful for restoration of circulation generally, including circulation compromised by chronic conditions such as diabetes, circulation to damaged tissues, and other similar disorders. Furthermore, the use of larger peptides containing active core sequences could potentially enhance the therapeutic benefits disclosed herein.

SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 1

Trp Asn Ser Thr Leu
1 5

<210> SEQ ID NO 2
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 2

Asn Gln His Thr Pro Arg
1 5

<210> SEQ ID NO 3
<211> LENGTH: 4
<212> TYPE: PRT
<213> ORGANISM: Artificial Sequence
<220> FEATURE:
<223> OTHER INFORMATION: linker peptide

<400> SEQUENCE: 3

Gly Gly Gly Ser
1

<210> SEQ ID NO 4
<211> LENGTH: 8
<212> TYPE: PRT
<213> ORGANISM: Artificial Sequence
<220> FEATURE:
<223> OTHER INFORMATION: linker peptide

<400> SEQUENCE: 4

Gly Gly Gly Ser Gly Gly Gly Ser
1 5

<210> SEQ ID NO 5
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 5

Trp Asn Ser Thr Tyr
1 5

<210> SEQ ID NO 6
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 6

Tyr Asn Ser Thr Leu
1 5

```
<210> SEQ ID NO 7
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 7

Tyr Gln Pro Ser Leu
1               5


<210> SEQ ID NO 8
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 8

Val Gln Ala Thr Gln Ser
1               5


<210> SEQ ID NO 9
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 9

Val Ser Asn Gln His
1               5


<210> SEQ ID NO 10
<211> LENGTH: 4
<212> TYPE: PRT
<213> ORGANISM: Artificial Sequence
<220> FEATURE:
<223> OTHER INFORMATION: linker peptide

<400> SEQUENCE: 10

Ser Ser Ser Ser
1


<210> SEQ ID NO 11
<211> LENGTH: 8
<212> TYPE: PRT
<213> ORGANISM: Artificial Sequence
<220> FEATURE:
<223> OTHER INFORMATION: linker peptide

<400> SEQUENCE: 11

Ser Ser Ser Ser Ser Ser Ser Ser
1               5
```

What is claimed is:

1. A therapeutic peptide consisting of between 5 to 6 amino acids [and] *having* a peptide sequence selected from the group consisting of:

X1-Q-X2-X3-X4-X5; and

X1-N-S-X3-X4-X5 wherein X1 is selected from the group consisting of N, V, W, and Y;

X2 is selected from the group consisting of H, A, and P;

X3 is selected from the group consisting of T[, Q,] and S;

X4 is selected from the group consisting of P, Q, [H,] L, and Y; and

X5 is selected from the group consisting of R and S, or is absent.

2. The therapeutic peptide of claim 1, in a substantially pure form of at least 80% by weight.

3. The therapeutic peptide of claim 1, wherein the N-terminus is acetylated and the peptide is pro-angiogenic.

4. A therapeutic composition comprising the therapeutic peptide of claim 1 and a pharmaceutically acceptable carrier.

5. A method of modulating a cytokine expression in a subject, the method comprising administering to a subject one or more therapeutic peptides of claim 1, wherein the therapeutic peptide is administered in an amount sufficient to modulate the expression of at least one endogenous cytokine.

6. The method of claim 5, wherein the at least one cytokine is selected from the group consisting of: Eotaxin, Eotaxin-2, ICAM-1, 1-309, IL-4, IL-8, IL-10, IL-11, IL-15, IL-16, IL-17, IL-21, RANTES, sTNF RI, sTNF RII, IL-12p40, IL-12p70, M-CSF, MCP-2, MIG, PDGF-BB, TNF-β, MIP-1b, GCSF, and TIMP-2.

7. The method of claim 5, wherein the therapeutic peptide increases the endogenous expression of at least one cytokine selected from the group consisting of: IL-11, IL-12p40, IL-12p70, RANTES, sTNF RI, PDGF-BB, Eotaxin, Eotaxin-2, IL-15, IL-16, IL-17, MCP-2, M-CSF, MIG, TNF-β, sTNF RII, and TIMP-2; and/or decreases the endogenous expression of at least one cytokine selected from the group consisting of: IL-7, IL-8, IL-10, Eotaxin-2, GCSF, ICAM-1, INF-γ, IL-6sR, TIMP-2, MCP-1, and MIP-1b.

8. A method of stimulating wound healing in a subject via induction of angiogenesis, the method comprising: administering the composition of claim 4 to the subject in an amount sufficient to stimulate angiogenesis of a wound area.

9. The method of claim 8, wherein the method comprises modulating the release of a profile of cytokines in the subject, comprising increasing the release in the subject of at least one therapeutically beneficial cytokine and/or inhibiting in the subject the production or release of at least one therapeutically deleterious cytokine.

10. The method of claim 9, further comprising stimulating the activity of phagocytic cells and modulating the immune system of that subject to further promote wound healing and decrease inflammation of a wound area.

11. The method of claim 9, wherein the cytokine profile released is indicative of a reduction of inflammation.

12. The method of claim 9, wherein the at least one beneficial cytokine is PDGF-BB and the at least one deleterious cytokine is IL-8.

13. The method of claim 9, wherein the administration of the composition enhances the ability of the immune system to ward off or attenuate infection at the wound.

14. The method of claim 9, wherein the amount is within the range of 1 pmole to 1 nmole per g of body weight of the subject.

15. The method of claim 9, wherein the amount administered is within the range of 0.1 to 300 mg per dose, and the dose is administered one or two times per week.

16. The method of claim 9, wherein the composition is in a formulation suitable for oral administration to the subject, the dosage designed to pass through the subject's stomach before releasing the peptide in the subject's intestine for absorption through the intestinal epithelium.

17. The method of claim 9, wherein the composition is administered via a patch comprising: polyethyleneglycol, propylene glycol, methyl paraben, ethyl paraben, hydroxypropylmethyl cellulose, DMSO, isopropyl myristate, mineral oil, white petrolatum, bees wax, or glycerine.

* * * * *